United States Patent [19]

Adrian et al.

[11] Patent Number: 4,739,100

[45] Date of Patent: Apr. 19, 1988

[54] PROCESS FOR PREPARING 6-(LOWER) ALKOXY-1-NAPHTHOIC ACIDS AND THE CORRESPONDING ESTERS AND USE OF THIS PROCESS FOR PREPARING 6-(LOWER) ALKOXY-5-HALO-1-NAPHTHOIC ACIDS AND THE CORRESPONDING ESTERS

[75] Inventors: Guy P. Adrian, Givors; Sylvain G. Garnier, Corbas - St Priest, both of France

[73] Assignee: Delalande S.A., Courbevoie, France

[21] Appl. No.: 780,902

[22] Filed: Sep. 27, 1985

[30] Foreign Application Priority Data

May 10, 1985 [FR] France ............................... 85 07107

[51] Int. Cl.$^4$ ............................................. C07C 69/76
[52] U.S. Cl. ..................................... 560/056; 562/467
[58] Field of Search ........................... 560/56; 562/467

[56] References Cited

PUBLICATIONS

Price, C. et al, JACS, vol. 63, 1941, pp. 1857–1861.

*Primary Examiner*—Paul J. Killos
*Attorney, Agent, or Firm*—Birch, Stewart, Kolasch & Birch

[57] ABSTRACT

The present invention provides a process for preparing 6-(lower)alkoxy-1-naphthoic acids, the corresponding esters and 5-halo substituted derivatives thereof. The process comprises reacting furoic acid with an alkoxyphenyl compound, followed by acid hydrolysis to form a mixture of alkoxy and hydroxy substituted naphthoic acids, subjecting said mixture to the action of an alkylating agent, and optionally further treating the alkylated product to another hydrolysis step or a halogenation step.

28 Claims, No Drawings

PROCESS FOR PREPARING 6-(LOWER) ALKOXY-1-NAPHTHOIC ACIDS AND THE CORRESPONDING ESTERS AND USE OF THIS PROCESS FOR PREPARING 6-(LOWER) ALKOXY-5-HALO-1-NAPHTHOIC ACIDS AND THE CORRESPONDING ESTERS

The present invention relates to a new process for preparing 6-(lower)alkoxy-1-naphthoic acids and the corresponding esters, as well as the use of this process for preparing 6-(lower)alkoxy-5-halo-1-naphthoic acids and the corresponding esters.

The acids and esters of this type form particularly useful synthesis intermediates for preparing different aldose reductase inhibitors which find their application in the treatment of complications in diabetes. These intermediates, the preparation thereof and transformation thereof into aldose reductase inhibitors are described more especially in J.A.C.S., 69, 2261 (1947), in U.S. Pat. No. 4,408,077 and in European patent application No. 00 59596.

The article published in J.A.C.S., 69, 2261 (1947) describes in particular the preparation of 6-methoxy-1-naphthoic acid and the corresponding methyl ester, by condensing anisole with furoic acid in the presence of aluminium chloride, followed by acid hydrolysis, isolation of the resulting acid and possible esterification by means of methanol of the thus isolated acid. As is stated in this article, the most satisfactory conditions for preparing said acid consist in operating in the presence of a considerable excess of anisole (10 equivalents) and in the absence of any other solvent, with a reaction time of 48 hours.

The applicant has however discovered that by repeating the operating mode proposed in this article, a pasty reaction mixture was obtained difficult to stir and thus difficult to homogenize and hydrolyse, 6-methoxy-1-naphthoic acid being obtained after fastidious isolating operations only with very low yields (of the order of 6 to 11% with respect to the starting furoic acid) and in the form of an impure product. All these disadvantages form then major obstacles to the industrial use of the process proposed in this article.

One of the aims of the present invention is consequently, to provide a process for preparing 6-(lower) alkoxy-1-naphthoic acids and the corresponding esters, with improved yields, under simple operating conditions easy to put into practice industrially.

The present invention concerns more precisely a process for preparing a compound of the formula:

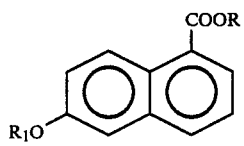 (I)

in which R=H or lower alkyl and $R_1$=lower alkyl, which comprises the reaction, in the presence of a condensation agent, of furoic acid with a compound of formula:

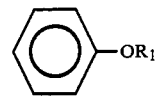 (II)

where $R_1$ has the same meaning as above, followed by acid hydrolysis, which leads to a reaction mixture comprising two compounds respectively of formula (III) and formula (IV):

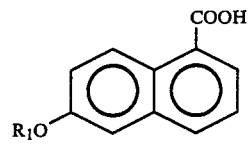 (III)

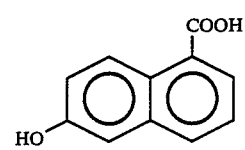 (IV)

where $R_1$ has the same meaning as before, this process being characterized in that it further comprises the action of an alkylating agent on compounds (III) and (IV) of said mixture and on these compounds in the form of salts, this alkylating agent being chosen so as to form the compound of formula:

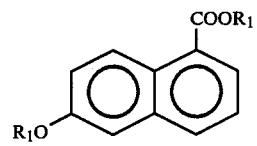 (Ia)

where $R_1$ has the same meaning as before and, if desired hydrolysis of the ester group of the compound (Ia) for obtaining the corresponding acid of formula:

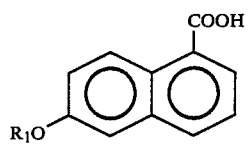 (III)

The applicant has in fact demonstrated for the first time that the ring closure condensation reaction between furoic acid and compound (II) did not lead, after acid hydrolysis, only to the acid (III) but in fact to a mixture containing the acid (III) and 6-hydroxyl-1-naphthoic acid (IV). In the process known from the above mentioned article in J.A.C.S. this acid (IV) was purely and simply eliminated during the operations for isolating and purifying the 6-methoxy-1-naphthoic acid, which is one of the reasons explaining the low yields with which the final ester is obtained.

On the contrary, rather than eliminating the acid (IV) the applicant has judiciously taken advantage of the presence of this acid for improving these yields, by subjecting the mixture of acid (III) and (IV) to the action of an alkylating agent chosen for transforming the 6-hydroxy radical of the acid (IV) into a lower alkoxy group, said alkylating agent being more precisely chosen for transforming the 6-hydroxy radical into a group $R_1O$ identical to that present in position 6 of the acid (III). For the same number of steps, the process of the invention thus allows the ester (Ia) to be obtained with yields appreciably greater than those obtained with the known process and which may reach values of the order of 30% with respect to the starting furoic acid.

It should be noted that the alkylating agent may be reacted directly with the reacting mixture resulting from the condensation of the furoic acid and compound (II) and the acid hydrolysis of the resultant condensation product. It is however preferable, previous to the action of said alkylating agent on the compounds (III) and (IV), for these latter to be separated from the reaction mixture. This separation may advantageously be achieved by extracting the reaction mixture at a pH of 7-9 by means of a basic agent in an aqueous medium, in which case the compounds (III) and (IV) are separated in the form of salts and reacted in this form with the alkylating agent. The basic agent may be formed for example by an alkali metal bicarbonate and in particular by potassium bicarbonate preferred because of its great solubility in water.

The alkylating agent may be chosen from the group comprising the lower alkyl halides, the lower alkyl sulphates, the di(lower alkyl) sulphates and mixtures thereof.

This alkylating agent is advantageously used in an aqueous medium or in a medium comprising water and a solvent chosen from acetone, methyl ethyl ketone, methylene chloride and 1,2-dichloroethane, and in the presence of a weak base such as a mineral base for example potassium carbonate.

The condensation agent used for the reaction of the furoic acid with the compound (II) is generally present at the rate of 3 to 5 moles per mole of furoic acid; it is formed by a Lewis acid of the $AlCl_3$ type, a part of this acid being optionally replaced by a dehydrating acid such as sulphuric acid, phosphoric acid, phosphoric anhydride and mixtures thereof.

The applicant has further demonstrated that if the condensation reaction of the furoic acid and compound (II) is carried out in a specific solvent chosen from the group comprising: the polyhalogenated aliphatic hydrocarbons such as 1,1,2,2-tetrachloroethane, the polyhalogenated aromatic hydrocarbons such as ortho dichlorobenzene and mixtures thereof, it is possible to substantially limit the parasite reaction of dealkylation of the compound (II) into phenol (a very considerable parasite reaction in the known process in which the major part of the excess anisole is transformed into phenol) and, therefore, to increase the yield of the condensation reaction. In addition to this particular effect, with the presence of this solvent lesser quantities of compound (II) can be used (4 to 8 equivalents only with respect to the furoic acid for 10 equivalents in the known process), the reaction mixture is very fluid and so easily stirrable and the reaction time is very much shortened since with times of 6 to 10 hours, under the above defined conditions, compounds of (III) and (IV) may be obtained with overall yields of the order of 30 to 40% with respect to the starting furoic acid.

The present invention also relates to the application of the process which has just been described to the preparation of 6-(lower) alkoxy-5-halo-1-naphthoic acids and the corresponding esters from furoic acid and compounds (II).

Consequently, the present invention extends to a process for preparing a compound of formula:

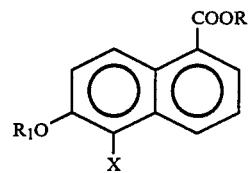

where $R$=H or lower alkyl, $R_1$=lower alkyl and $X$=halogen, consisting in preparing the compound of formula:

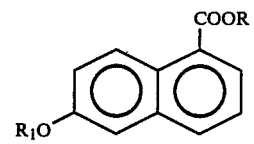

where $R_1$ and $R$ have the same meaning as in formula (V) from furoic acid and the compound of formula:

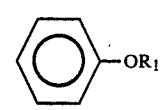

where $R_1$=lower alkyl, then in treating the compound (I) thus obtained by means of a halogenating agent, this process being characterized in that the compound (I) is prepared in accordance with the process defined in the preceding description from furoic acid and compound (II).

Halogenation of compound (I) may be performed under the conditions described for example in European patent application No. 00 59596 or in U.S. Pat. No. 4,408,077 using chlorine, bromine or iodine. It is further possible to effect this reaction in a water/halogenated aliphatic hydrocarbon medium such as water/1,2-dichloroethane preferably at a low temperature so as to avoid polyhalogenation of the naphthalene nucleus, more especially at 0°-30° C.

The resulting halogenated compounds (V) are then isolated and purified in a conventional way.

In compound (V), where R is lower alkyl, the corresponding compound is illustrated by the formula:

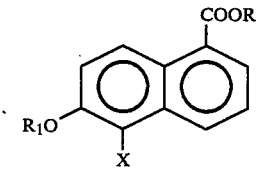

where $R_1$, R and X have the same meaning as in formula (V) and where R is H, the corresponding compound is illustrated by the formula:

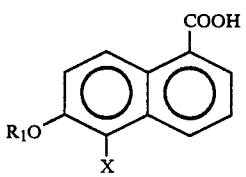

where $R_1$ and X have the same meaning as in formula (V).

The following examples are given for illustrating the invention and relate in particular to the preparation of the methyl ester of 6-methoxy-5-halo-1-naphthoic acid.

EXAMPLE 1

In a one liter reactor, equipped with a stirring device with rotating anchor (350 rpm) are placed 56 g (0.5 mole) of furoic acid, 270 g of anisole (2.55 moles) and 187 ml of ortho dichlorobenzene.

The mixture is heated to 40° C. and within 5 hours, 30 charges of 9 g of aluminium chloride (2 moles) are introduced at the rate of one charge every 10 minutes.

The whole is heated to 80° C. for 3.5 hours and the viscous medium is then diluted with 100 g of anisole and 70 ml of ortho dichlorobenzene at 80° C. and stirred for 1 hour then hydrolysed with 1500 ml of 6N hydrochloric acid.

Between 60° and 65° C., 250 ml of isopropyl acetate are added to the medium and after leaving it to decant 922 g of an upper organic phase was obtained containing, by weight, 2.61% of 6-methoxy-1-naphthoic acid and 1.30% of 6-hydroxy-1-naphthoic acid.

This organic solution was extracted at 60° C. with 400 ml of a saturated potassium bicarbonate solution (350 g per liter) so as to give an aqueous phase containing the salts of these two naphthoic acids. These acids were released using hydrochloric acid with a pH of 1.2. extracted at 60° C. using 300 ml of 1,2-dichloroethane and methylated using 77.5 ml (0.82 Mole) of dimethyl sulphate in the presence of 108 g, (0.78 mole) of potassium carbonate and 500 ml of acetone, between 30° and 60° C., for three hours.

After eliminating the acetone by distillation, the remaining reaction medium was washed using two fractions of 500 ml of water, then treated using 67 g of bromine (0.417 mole) at 25° C. in the presence of 100 ml of water.

After two hours reaction time, the organic phase was separated by decantation, then concentrated in a vacuum at 50° C.; by adding to the residue a mixture of 130 ml of isopropyl acetate and 60 ml of isopropanol, at 0° C., by crystallization then by drying 40 g were obtained of methyl 6-methoxy-5-bromo-1-naphthoate (melting point: 127° C.; LGC purity: 99–100%; yield: 27% with respect to the starting furoic acid).

EXAMPLE 2

The operating mode of example 1 was repeated but by replacing the ortho dichlorobenzene by an equivalent amount of 1,1,2,2-tetrachloroethane.

38 g (yield: 25.8%) were finally obtained of methyl 6-methoxy-5-bromo-1-naphthoate.

EXAMPLE 3

As in example 1, 56 g of furoic acid and 270 g of anisole were reacted in the presence of 187 ml of ortho dichlorobenzene, at 40° C., with introduction of 20 charges of 9 g of aluminium chloride (1.35 mole) at the rate of one charge every 10 minutes, then of 49 g of concentrated sulphuric acid (0.5 mole).

The experiment was then continued as for example 1 to obtain 896 g of an organic phase containing 2.71% by weight of 6-methoxy-1-naphthoic acid and 0.77% by weight of 6-hydroxy-1-naphthoic acid. After methylation and bromation carried out as for Example 1, 32.5 g of methyl 6-methoxy-5-bromo-1-naphthoate were obtained (yield: 22.5%).

EXAMPLE 4

In a reactor of 6 m³ are placed 250 kg of furoic acid, 1210 liters of anisole and 835 liters of ortho dichlorobenzene. The mixture is heated to 42° C. and, while maintaining this temperature, 1200 kg of aluminium chloride, are added over 5.5 hours (33 charges of 36.36 kg at the rate of one charge every 10 minutes).

The reaction was fairly exothermic during the first half of the introduction. The temperature is held at 42° C. for ten minutes, then the mixture is heated to 82° C. over 30 minutes and this temperature is held for three hours 40 minutes. Then 445 liters of anisole and 307 liters of ortho dichlorobenzene were added.

The mixture is kept at 82° C. for 30 minutes, cooled to 65°–70° C. and poured over a mixture of 2875 liters of water and 2875 liters of 12.5N HCl without exceeding 80° C.

The reactor was rinsed with 1000 liters of isopropyl acetate, the resultant mixture was added to the hydrolysis medium, the whole was stired for 15 minutes at 65° C., then decanted. The lower aqueous phase was eliminated, the upper organic phase (weight ≃3900 kg) was retained which contains ≃2.6% of 6-methoxy-1-naphthoic acid and ≃1.6% of 6-hydroxy-1-naphthoic acid (overall acid yield: 36–38%). This phase was subjected to three extractions at 80° C. respectively with 1340 liters, 223 liters and 223 liters of a saturated aqueous solution of $KHCO_3$ (400 g/1100 ml) and the lower aqueous phases were combined so as to obtain an aqueous solution of potassium salts of the two above acids.

In a reactor of 6 m³, are charged 2200 liters of acetone, 520 kg of $K_2CO_3$ and 380 liters of $(CH_3)_2SO_4$.

The resultant mixture was stirred and the aqueous solution of the previously obtained potassium salts was added thereto. The whole was heated to reflux until said salts disappeared (check by TLC), which result was obtained after about 3 hours.

The acetone was evaporated at atmospheric pressure until a vapor at 100° C. was obtained. The remaining mixture was cooled to 60° C. and 2000 liters of water were added thereto, extraction was carried out using 2 fractions of 500 liters of 1,2-dichloroethane, the dichloroethane phases were combined which contained ≃125 kg of methyl 6-methoxy-1-naphthoate (yield ≃29% with respect to the starting furoic acid). Then the dichloroethane solution (about 1300–1400 liters) was charged in a reactor of 3 m³, 350 liters of water were added, the whole was stirred at 20°–25° C. and 130 liters of bromine (exothermic reaction) were added while maintaining the medium at a maximum temperature of 25° C. Stirring was carried out for an hour after the end of introducing the bromine (determination of the disappearance of the methyl ester of 6-methoxy-1-naphthoic acid by LGC on a sample of the lower organic phase).

The lower organic phase was separated by decantation and washed with 450 liters of water.

The washed organic phase was separated, the solvent evaporated (in a vacuum at the end of evaporation) and the residue was taken up in a mixture of 600 liters of isopropyl acetate and 300 liters of isopropylic alcohol.

The whole was then heated until complete dissolution at about 60° C., then cooled and chilled at 5° C. for two hours.

The precipitate formed was separated by filtration, dried for example in a centrifugal drier, washed using a chilled mixture of 50 liters of isopropyl acetate and 100 liters of isopropylic alcohol and dried at 60° C., which gave 165–170 kg of 6-methoxy-5-bromo-1-naphthoic acid methyl ester (yield with respect to the starting furoic acid: about 25%).

EXAMPLE 5

The same condensation and methylation reactions were carried out as for example 1; then 35.5 g of chlorine (0.5 mole) were reacted on the crude methyl 6-methoxy-1-naphthoate obtained, at 20° C. in the presence of 100 ml of water for 5 hours.

After decantation, the organic phase was concentrated in a vacuum at 50° C. and the residue was crystallized in 150 ml of isopropanol, at 0° C., to give 31.3 g of methyl 6-methoxy-5-chloro-1-naphthoate which is a new compound.

Melting point: 125° C.

Yield with respect to the starting furoic acid: 25%.

IR spectrum: 1715 cm$^{-1}$ (COO).

NMR spectrum (CDCl$_3$),: 3.97 (s, 3H); 4.05 (s, 3H); 7.3–9.0 (m, 6H).

EXAMPLE 6

The same condensation and methylation reactions were carried out as for example 1; then 53 g of iodine and 20 g of iodic acid were reacted on the crude methyl 6-methoxy-1-naphthoate solution obtained, in the presence of 200 ml of acetic acid and 200 ml of an N/2 sulphuric acid solution, for five hours.

After decantation, the organic phase was washed with a solution of 10 g of sodium thiosulphate in 200 ml of water then concentrated in a vacuum at 50° C. and the residue was crystallized in 150 ml of isopropanol, at 0° C.

Thus 36 g of methyl 6-methoxy-5-iodo-1-naphthoate were obtained (melting point: 100° C. yield with respect to the furoic acid: 21%).

We claim:

1. A process for preparing a compound of the formula:

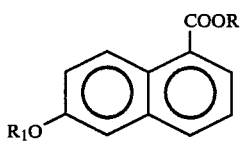

in which R$_1$ and R are lower alkyl, which comprises reacting furoic acid with a compound of the formula:

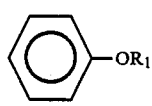

in the presence of a condensation agent to form condensates, wherein R$_1$ has the same meaning as above, acid hydrolyzing the condensates to form a mixture comprising compounds of formulae (III) and (IV):

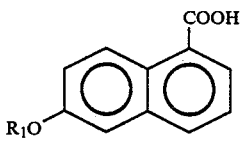

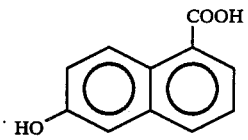

wherein R$_1$ has the same meaning as above, and subjecting the mixture comprising compounds of formulae (III) and (IV) or salts thereof to an alkylation reaction by means of an alkylating agent to form the compound of the formula (Ia).

2. The process of claim 1, wherein compounds of formulae (III) and (IV) are separated from the mixture prior to being subjected to the alkylation reaction.

3. The process of claim 2, wherein the separation is effected by extracting the compounds of formulae (III) and (IV) from the mixture at a pH of 7–9 by means of a basic agent in an aqueous medium.

4. The process of claim 3, wherein the basic agent is an alkali metal bicarbonate.

5. The process of claim 1, wherein the alkylating agent is selected from the group consisting of lower alkyl halides, lower mono-alkyl sulfates, lower di-alkyl sulfates and mixtures thereof.

6. The process of claim 5, wherein the alkylation reaction is conducted in an aqueous medium or a medium comprising a mixture of water and a solvent selected from the group consisting of acetone, methyl ethyl ketone, methylene chloride and 1,2-dichloroethane.

7. The process of claim 1, wherein the alkylating reaction is conducted in the presence of a weak base.

8. The process of claim 1, wherein the condensation agent comprises a mixture of aluminum chloride and a dehydrating acid.

9. The process of claim 8, wherein the dehydrating acid is selected from the group consisting of sulphuric acid, phosphoric acid, phosphoric anhydride and mixtures thereof.

10. The process of claim 1, wherein the reaction of furoic acid and the compound of formula II is conducted in the presence of a solvent selected from the group consisting of polyhalogenated aliphatic hydrocarbons, polyhalogenated aromatic hydrocarbons and mixtures thereof.

11. The process of claim 10, wherein the polyhalogenated aliphatic hydrocarbon is 1,1,2,2-tetrachloroethane and the polyhalogenated aromatic hydrocarbon is ortho-dichlorobenzene.

12. The process of claim 1, wherein R$_1$ of formula (Ia) is methyl, the compound of formula (II) is anisole and the alkylating agent is a methylating agent.

13. A process for preparing a compound of the formula:

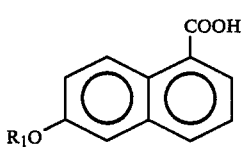

in which R$_1$ is lower alkyl, which comprises reacting furoic acid with a compound of formula:

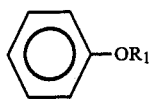

in the presence of a condensation agent to form condensates, wherein $R_1$ has the same meaning as above, acid hydrolyzing the condensates to form a mixture comprising compounds of formulae (III) and (IV):

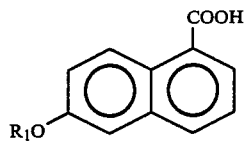

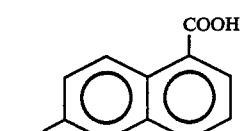

wherein $R_1$ has the same meaning as above, subjecting the mixture comprising compounds of formulae (III) and (IV) or salts thereof to an alkylation reaction by means of an alkylating agent to form the compound of the formula (Ia), and hydrolyzing the compound of the formula (Ia) to form the compound of the formula:

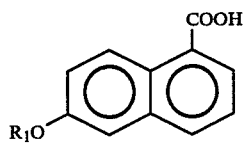

wherein $R_1$ has the same meaning as above.

14. The process of claim 13, wherein compounds of formulae (III) and (IV) are separated from the mixture prior to being subjected to the alkylation reaction.

15. The process of claim 14, wherein the separation is effected by extracting the compounds of formulae (III) and (IV) from the mixture at a pH of 7-9 by means of a basic agent in an aqueous medium.

16. The process of claim 15, wherein the basic agent is an alkali metal bicarbonate.

17. The process of claim 13, wherein the alkylating agent is selected from the group consisting of lower alkyl halides, lower mono-alkyl sulfates, lower di-alkyl sulfates and a mixtures thereof.

18. The process of claim 17, wherein the alkylation reaction is conducted in an aqueous medium or a medium comprising a mixture of water and a solvent selected from the group consisting of acetone, methyl ethyl ketone, methylene chloride and 1,2-dichloroethane.

19. The process of claim 13, wherein the alkylating reaction is conducted in the presence of a weak base.

20. The process of claim 13, wherein the condensation agent comprises a mixture of aluminum chloride and a dehydrating acid.

21. The process of claim 20, wherein the dehydrating acid is selected from the group consisting of sulphuric acid, phosphoric acid, phosphoric anhydride and mixtures thereof.

22. The process of claim 13, wherein the reaction of furoic acid and the compound of formula II is conducted in the presence of a solvent selected from the group consisting of polyhalogenated aliphatic hydrocarbons, polyhalogenated aromatic hydrocarbons and mixtures thereof.

23. The process of claim 22, wherein the polyhalogenated aliphatic hydrocarbon is 1,1,2,2-tetrachloroethane and the polyhalogenated aromatic hydrocarbon is ortho dichlorobenzene.

24. The process of claim 13, wherein $R_1$ of formula (I) is methyl, the compound of formula (II) is anisole and the alkylating agent is a methylating agent.

25. A process for preparing a compound of the formula:

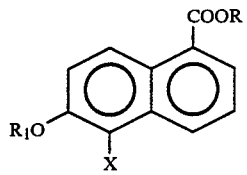

wherein $R_1$ and R are lower alkyl and X is halogen, which comprises subjecting a compound of the formula:

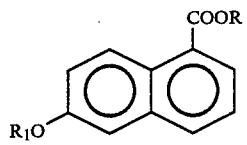

wherein $R_1$ and R have the same meaning as above and in which said compound of formula (Ia) is prepared in accordance with the process of claim 15, to a halogenation reaction by a halogenation agent to form the compound of formula (Va).

26. The process of claim 23, wherein the halogenation reaction is conducted in the presence of a medium comprising a mixture of water and a halogenated aliphatic hydrocarbon.

27. A process for preparing a compound of formula:

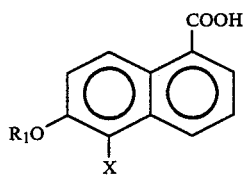

wherein $R_1$ = lower alkyl and X = halogen, which comprises subjecting a compound of the formula:

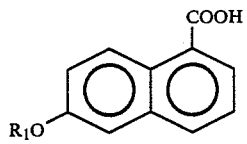

wherein $R_1$ has the same meaning as above and in which said compound of the formula (Ib) is prepared in accordance with the process of claim 27, to a halogenation reaction by a halogenating agent to form the compound of formula (Vb).

28. The process of claim 25, wherein the halogenation reaction was conducted in the presence of a medium comprising a mixture of water and a halogenated aliphatic hydrocarbon.

* * * * *